(12) United States Patent
O'Halloran

(10) Patent No.: US 8,871,921 B2
(45) Date of Patent: Oct. 28, 2014

(54) DESIGN, SYNTHESIS AND USE OF SYNTHETIC NUCLEOTIDES COMPRISING CHARGE MASS TAGS

(75) Inventor: Jonathan O'Halloran, Uckfield (GB)

(73) Assignee: Quantumdx Group Ltd., Newcastle (GB)

( * ) Notice: Subject to any disclaimer, the term of this patent is extended or adjusted under 35 U.S.C. 154(b) by 249 days.

(21) Appl. No.: 13/062,206

(22) PCT Filed: Sep. 3, 2009

(86) PCT No.: PCT/IB2009/007025
§ 371 (c)(1),
(2), (4) Date: Mar. 3, 2011

(87) PCT Pub. No.: WO2010/026490
PCT Pub. Date: Mar. 11, 2010

(65) Prior Publication Data
US 2011/0165563 A1    Jul. 7, 2011

Related U.S. Application Data

(60) Provisional application No. 61/094,025, filed on Sep. 3, 2008.

(51) Int. Cl.
| C07H 19/04 | (2006.01) |
| B01L 3/00  | (2006.01) |
| C12Q 1/68  | (2006.01) |
| C07H 21/00 | (2006.01) |
| C12P 19/34 | (2006.01) |

(52) U.S. Cl.
USPC ......... 536/26.6; 536/23.1; 536/24.3; 435/6.1; 435/91.1; 422/430

(58) Field of Classification Search
USPC ............... 435/6.1, 91.1; 536/23.1, 24.3, 26.6; 422/430
See application file for complete search history.

(56) References Cited

U.S. PATENT DOCUMENTS

| 6,310,189 | B1 | 10/2001 | Fodor et al. |
| 2001/0036672 | A1 | 11/2001 | Anderson et al. |
| 2003/0104437 | A1 | 6/2003 | Barnes et al. |
| 2003/0215816 | A1* | 11/2003 | Sundararajan et al. ........... 435/6 |
| 2005/0123958 | A1 | 6/2005 | Tsuchiya |
| 2005/0164205 | A1 | 7/2005 | Puskas |
| 2007/0190546 | A1 | 8/2007 | Siddiqi et al. |
| 2007/0238186 | A1 | 10/2007 | Sun et al. |
| 2010/0093992 | A1 | 4/2010 | Cherkasov et al. |

FOREIGN PATENT DOCUMENTS

| CN | 1617937 | 5/2005 |
| CN | 10184853 | 5/2008 |
| JP | 2005-503114 | 2/2005 |
| JP | 2005-511058 | 4/2005 |
| JP | 2005-526512 | 9/2005 |
| JP | 2007-195548 | 8/2007 |
| JP | 2008-534018 | 8/2008 |
| WO | WO 97/28282 A1 | 8/1997 |
| WO | WO 02/063030 A2 | 8/2002 |
| WO | 03048387 | 6/2003 |
| WO | WO 03/052139 A1 | 6/2003 |
| WO | WO 03/091406 A2 | 11/2003 |
| WO | WO 03/100096 A1 | 12/2003 |
| WO | 2006001944 A1 | 1/2006 |
| WO | WO 2006/095981 A1 | 9/2006 |
| WO | WO 2006/097320 A2 | 9/2006 |
| WO | WO 2006/105360 A1 | 10/2006 |
| WO | 2007062160 | 5/2007 |
| WO | WO 2007/077952 A1 | 7/2007 |
| WO | 2008079169 A2 | 7/2008 |
| WO | WO 2009/006445 A2 | 1/2009 |

OTHER PUBLICATIONS

Stratagene Catalog 1988, p. 39.*
Kumar et al. Nucleosides, Nucleotides, and Nucleic Acids, 24 pp. 401-408, 2005.*
Costa et al., Characterization in vitro and in vivo of the putative multigene 4-coumarate: CoA ligase network in *Arabidopsis*: syringyl lignin and sinapate/sinapyl alcohol derivative formation, Phytochemistry, Sep. 1, 2005, vol. 66, No. 17, pp. 2072-2091.
International Search Report dated Mar. 3, 2010, for International Application No. PCT/IB2009/006976.
International Search Report dated Feb. 19, 2010, for International Application No. PCT/IB2009/005008.
International Search Report dated Feb. 17, 2010, for International Application No. PCT/IB2009/007025.
Maki, W.C. et al., Universal bio-molecular signal transduction-based nano-electronic bio-detection system, Sensors and Actuators B, Aug. 12, 2008, vol. 133, No. 2, pp. 547-554.
Star, A. et al., Label-free detection of DNA hybridization using carbon nanotube network field-effect transistors, Proceedings of the National Academy of Sciences of USA, Jan. 24, 2006, vol. 103, No. 4, pp. 921-926.
Wu, F. Y.-H. et al., Synthesis and properties of adenosine-5'-triphosphoro-gamma-1-(5-sulfonic acid)naphthyl ethylamidate: A fluorescent nucleotide substrate for DNA-dependent RNA polymerase from *Escherichia coli*, Archives of Biochemistry and Biophysics, May 1, 1986, vol. 246, No. 2, pp. 564-571.
Zhu, Z. et al., Molecular mechanism controlling the incorporation of fluorescent nucleotides into DNA by PCR, Cytometry, Jan. 1, 1997, vol. 28, pp. 206-211.

* cited by examiner

*Primary Examiner* — Jezia Riley
(74) *Attorney, Agent, or Firm* — Knobbe, Martens, Olson & Bear, LLP

(57) ABSTRACT

Embodiments of the present disclosure relate generally to reporter compositions which are synthetic nucleotides that comprise nucleotides with a high charge mass moiety attached thereto via a linker molecule. The linker molecules can vary in length in part to enable the high charge mass moiety to extend out from a DNA polymerase complex so that polymerization may not be influenced.

28 Claims, No Drawings

DESIGN, SYNTHESIS AND USE OF SYNTHETIC NUCLEOTIDES COMPRISING CHARGE MASS TAGS

CROSS REFERENCE TO RELATED APPLICATIONS

This application is the national phase under 35 U.S.C. §371 of prior PCT International Application No. PCT/IB2009/007025 which has an International filing date of Sep. 3, 2009, designating the United States of America, which claims the benefit of U.S. Provisional Patent Application No. 61/094,025 filed on Sep. 3, 2008, the disclosures of which are hereby expressly incorporated by reference in their entirety and are hereby expressly made a portion of this application.

BACKGROUND OF THE INVENTION

1. Field of the Invention

Some embodiments of the present disclosure relate generally to synthetic nucleotides that comprise nucleotides with a charge mass reporter molecule via a long linker molecule. The linker molecules can vary in length in part to enable the reporter moiety to extend out from the DNA Polymerase complex so that some aspects of polymerization may not be influenced entirely or partially.

2. Description of the Related Art

A nucleotide can be defined as a phosphate ester of a nucleoside, comprising a purine or pyrimidine base linked to ribose, or deoxyribose phosphates. The purine nucleotides having chiefly Adenine (A) or Guanine (G) as the base, the pyrimidine nucleotides Cystine (C), Thymoine (T) or Uracil (U), and which are the basic repeating units in DNA and RNA (Henderson's dictionary of biological terms, 1989).

DNA is a long polymer comprising units of deoxyribose nucleotides and RNA is a polymer of ribose nucleotides. This sequence of nucleotide bases can determine individual hereditary characteristics.

The central dogma of molecular biology generally describes the normal flow of biological information: DNA can be replicated to DNA, the genetic information in DNA can be 'transcribed' into mRNA, and proteins can be translated from the information in mRNA, in a process called translation, in which protein subunits (amino acids) are brought close enough to bond, in order (as dictated by the sequence of the mRNA & therefore the DNA) by the binding of tRNA (each tRNA carries a specific amino acid dependant on it's sequence) to the mRNA.

SUMMARY OF THE INVENTION

A reporter composition is disclosed in accordance with embodiments of the present invention. The reporter composition comprises a nucleotide or its derivative, a linker molecule, which may be attached to the nucleotide or its derivative, and a high charge mass moiety, which comprises a charge mass that is sufficient to change a property of a sensitive detection nanostructure operably coupled to the reporter composition. In some embodiments, the nucleotide or its derivative present in the reporter composition may be selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

In some other embodiments, the linker molecule comprises a molecule of the following general formula, $H_2N-L-NH_2$, wherein L may comprise a linear or branched chain comprising an alkyl group, an oxy alkyl group, or the combination thereof. L in the linker may comprise a linear chain comprising an alkyl group, an oxy alkyl group, or the combination thereof and a number of the alkyl group, the oxy alkyl group, or the combination thereof in the linear chain is 1 to 100, 1 to 75, 1 to 50, 1 to 25 or 1 to 1000 in various examples. In some examples, the number of the alkyl group, the oxy alkyl group, or the combination thereof in the linear chain can be more than 1000. The linker molecule and/or the high charge mass moiety is configured not to affect nucleotide polymerization by a polymerase and also be removable. The linker molecule can be linked to a phosphate group, sugar group or base of the nucleotide or its derivative.

In some embodiments, the high charge mass moiety present in the reporter composition can be positive or negative, and further the charge mass of moiety can be variable depending on pH. In some examples, the high charge mass moiety may comprise an aromatic and/or aliphatic skeleton, wherein the skeleton comprises one ore more of a tertiary amino group, an alcohol hydroxyl group, a phenolic hydroxy group, and any combinations thereof. In some examples, the high charge mass moiety comprises one or more of the following groups, any derivatives thereof, and any combinations thereof:

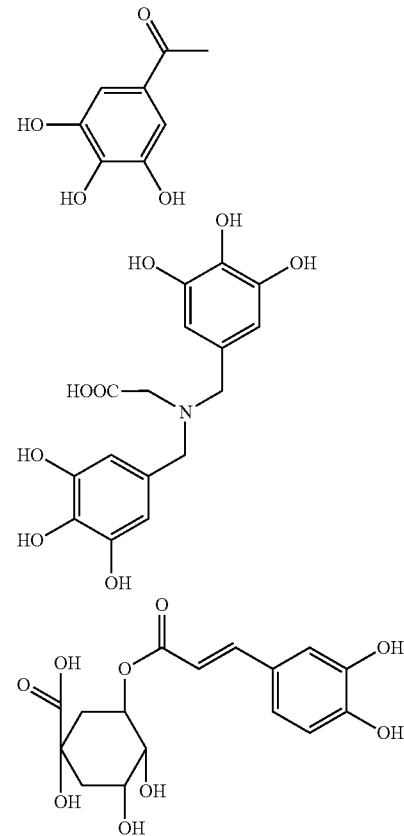

In addition, the number of the foregoing groups, any derivatives thereof, and any combinations thereof present in the high charge mass moiety can be 1 to 10, 11 to 50, 51 to 100, or more than 100 in various embodiments.

In one aspect of the invention, a reporter composition may comprise the following molecule:

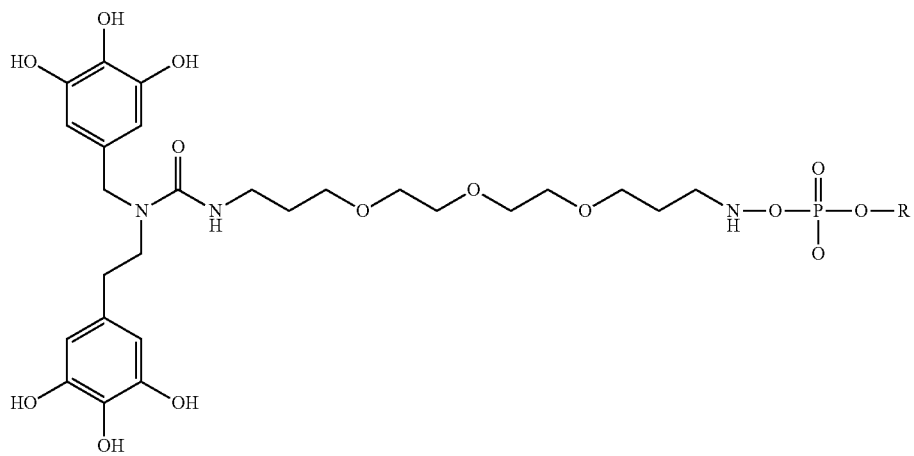

wherein, R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

In another aspect of the invention, a reporter composition may comprise the following molecule:

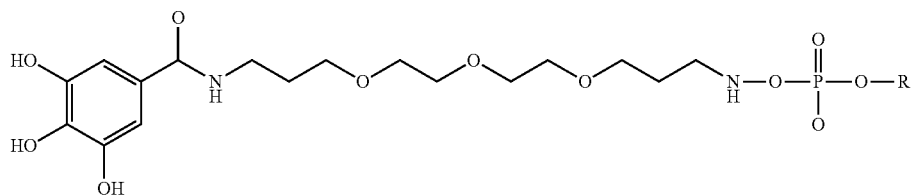

wherein, R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

In still another aspect of the invention, a reporter composition may comprise the following molecule:

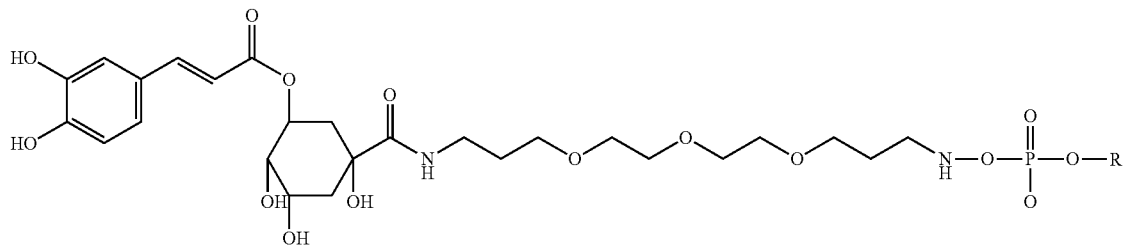

wherein, R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

A kit for determining a nucleotide sequence, comprising the reporter composition comprising a nucleotide or its derivative, a linker molecule, and a high charge mass moiety is also disclosed in accordance with embodiments of the present invention.

A method of synthesizing the reporter composition is also disclosed. The method comprises: generating a first covalent linkage between the nucleotide or its derivative and a first amine group of the linker, wherein a phosphate group, a sugar or a base of the nucleotide or its derivative is linked to the first amine group of the linker; and generating a second covalent linkage between a second amine group of the linker and any functional group present in the high charge mass moiety: wherein the linker comprises at least two amine groups is also disclosed in connection with the present application. In some embodiments, the nucleotide or its derivate used in the method may comprises a monophosphate group. In some other embodiments, the nucleotide or its derivate used in the method may be selected from the group consisting of adenosine monophosphate (AMP), guanosine monophosphate (GMP), cytidine monophosphate (CMP), thymidine monophosphate (TMP), and uridine monophosphate (UMP).

DETAILED DESCRIPTION OF THE PREFERRED EMBODIMENT

The sequencing of the human genome and the subsequent studies have since demonstrated the great value in knowing the sequence of a person's DNA. The information obtained by genomic DNA sequence analysis can provide information about an individual's relative risk of developing certain diseases (such as breast cancer and the BRCA 1&2 genes). Furthermore, the analysis of DNA from tumors can provide information about stage and grading.

Infectious diseases, such as those caused by viruses or bacteria also carry their genetic information in nucleotide polymer genomes (either DNA or RNA). Many of these have now been sequenced, (or enough of their genome sequenced to allow for a diagnostic test to be produced) and the analysis of infectious disease genomes from clinical samples (a field called molecular diagnostics) has become one of important methods of sensitively and specifically diagnosing disease.

Measurements of the presence or absence, as well as the abundance of mRNA species in samples can provide information about the health status of individuals, the disease stage, prognosis and pharmacogenetic and pharmacogenomic information. These expression arrays are fast becoming tools in the fight against complex disease and may gain in popularity as prices begin to fall.

In short, the analysis of nucleotide polymers (DNA & RNA) has become important in the clinical routine, however, cost remains a barrier to widespread global adoption. One reason for this is the complexity of the analysis requiring expensive devices that are able to sensitively measure up to four different fluorescence channels as RT-PCR experiments progress. The cheaper alternatives may require skilled technicians to run and interpret low-tech equipment, such as electrophoresis gels, but this too may be expensive and a lack of skilled technicians in developing countries is prohibitive.

To solve this, a method of nucleotide polymer analysis that may require cheap and easy to use devices may be required. Some embodiments of the present disclosure describes chemical reagents, synthetic nucleotides, that can generally be utilized in such devices. Various embodiments used in connection with of the present disclosure describes novel synthetic nucleotides that comprises at least some standard nucleotides (or any modifications, or isoforms), with a high negative charge mass reporter moiety attached via a linker molecule (for instance, attached to the 5' phosphate group), with the linker length of such a length so as to protrude from a polymerase complex during polymerization, so as not to cause a significant deleterious effect on the polymerase's action.

As used in various embodiments herein, a nucleotide can be, but not limited to, one of the following compounds, Adenine, Guanine, Cytosine, Thymine, Uracil, and Inosine as well as any modified nucleotides, any nucleotide derivatives and any degenerate base nucleotides. Some non-limiting examples of such nucleotide may comprise a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof. Furthermore, single stranded deoxyribose nucleic acid (ssDNA) can generally be a single stranded nucleotide polymer molecule, comprising Nucleotides and double stranded deoxyribose nucleic acid (dsDNA) can generally be a double strand comprising two ssDNA molecules linked together via, for example, hydrogen bonding, in a reverse complimentary orientation.

Nucleotides can generally be synthesized through a variety of methods both in vitro and in vivo. This can involve salvage synthesis (the re-use of parts of nucleotides in resynthesizing new nucleotides through breakdown and synthesis reactions in order to exchange useful parts), or the use of protecting groups in a laboratory. In the latter case, a purified nucleoside or nucleobase can be protected to create a phosphoramidite, and can be used to obtain analogues not present in nature and/or to create an oligonucleotide.

In some embodiments, nucleotide synthesis comprises the formation of a nucleoside (the nitrogenous base joined to a sugar). The sugar involved in the synthesis and structure of a nucleotide may be either ribose or deoxyribose; in the latter case, the prefix 'deoxy' may be added before the name of the nucleoside in all cases except Uracil. A functional group of phosphate can be then esterified to the sugar, creating a nucleotide. The phosphate group may comprise one, two, or three phosphates, forming mono-phosphates, di-phosphates, or tri-phosphates, respectively.

Some other embodiments of the present disclosure describe the design, synthesis and use of special synthetic nucleotides comprising a nucleotide and a reporter moiety, in which the reporter moiety may not act as a polymerase enzyme blocking moiety attached via a linker.

A reporter moiety or reporter composition used in various embodiments in connection with the present inventions is a molecule or molecules that are easily detected by a biosensor or other detection method (such as by eye) and are attached to biomolecules, or probes, or primers that detect or amplify molecules of interest.

A linker molecule used in various embodiments is a polymer made up of more than one subunit that links a reporter molecule to a nucleotide. An example of a linker molecule is a Di-amine linker $H_2N-L-NH_2$, where L represents a number of further subunits.

As such, the present disclosure should be considered to include all configurations that include any nucleotide or its derivative with a linker molecule attaching a reporter moiety with an overall high charge, sufficient enough to get a detectable change in a sensitive biosensor that can detect small variations in charge mass at or near its surface. Accordingly several examples presented in this application are presented only for the purpose of illustration and should not be considered to limit the scope of the invention.

In various embodiments, the synthetic nucleotides can have at least some of the following aspects:
1. The reporter moieties reports based upon its charge mass, not enzymatic activity, fluorescence etc;
2. Each synthetic nucleotide may either carry the same charge mass reporter moiety, or carry a different charge mass;
3. The reporter moieties may be easily cleaved; and/or
4. The nucleotides may be cheaply and easily mass synthesized.

There are several possible positions available for the attachment of linkers and the reporter moieties. It is important to attach the linker so as to not interfere with polymerization or hydrogen bonding between the bases of nucleotides when hybridizing with its compliment base in another nucleotide polymer (i.e. when two strands of reverse compliment DNA hybridize to form a double stranded DNA molecule), One possible position can be the phosphate linkage in the nucleotide. Furthermore, by attaching the linker to the 5' position in the phosphate, it will block further nucleotide additions as it will prevent phosphodiester bond formation.

Another possible positions available for the attachment of linkers and the reporter moieties, is on either the sugar group or the base group.

Some other embodiments describe methods of the use in which the linker and reporter moiety can be cleaved from the synthetic nucleotide in the iterative manner after detection. As one of the possible places to attach the linker is the 5'-phosphate end of phosphate group, which will prevent further nucleotide additions then, by cleaving the linker will therefore remove this block and allow for further nucleotide additions.

As way of an example, there are at least two options available which could facilitate synthesis at the 5'-phosphate terminal:

1. Thiophosphate; and/or
2. Phosphoramidate.

The proposed linker therefore can have the following structure at least in some embodiments:

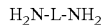

where, L could be, but is not limited to, any linear or branched chain molecule that is configured to link to a nucleotide as well as a high charge mass moiety, both of which are present in a synthetic nucleotide. In some embodiments, L comprises a plurality of an alkyl group, an oxy alkyl group or the combination thereof with various lengths. In one embodiment, the number of an alkyl group, an oxy alkyl group or the combination thereof in L is 1 to 100. In another embodiment, the number of an alkyl group, an oxy alkyl group or the combination thereof in L is 1 to 75. In still another embodiment, the number of an alkyl group, an oxy alkyl group or the combination thereof in L is 1 to 50. In still embodiment, the number of an alkyl group, an oxy alkyl group or the combination thereof in L is 1 to 25. In some other embodiments, the number of an alkyl group, an oxy alkyl group and the combination thereof in L can be more than 100. While $NH_2$ is presented for the purpose of illustration, this $NH_2$ can be substituted with any other function group that can be cross-linked to a nucleotide or its derivative as well as a high charge mass moiety, both of which are present in a synthetic nucleotide. Some illustrative examples that can be used instead of $NH_2$ include, but not limited to, any alkyl group (e.g. $C_nH_{2n+1}$, wherein n represents a positive integer number such as 1, 2, 3, and etc), any alcohol group (e.g. $C_nH_{2n}OH$, wherein n represents a positive integer number such as 1, 2, 3, and etc), any carboxyl group (e.g. COOH), any amide group (e.g. CONH), and any derivatives thereof. As the linker molecules can vary in length and chemical structure in part to enable the reporter moiety to extend out from a nucleotide polymerase (e.g. DNA polymerase, RNA polymerase and others) complex so that some aspects of polymerization may not be influenced entirely or partially The easy access to the linkers of various lengths can be considered as a benefit in a situation where the desired length of the linker may not be known completely or partially. This may make the optimization experiments easy.

The linker with the nucleotide (say Adenosine as an illustrative example) therefore may have the following structure at least in some embodiments. While adenosine is presented in some examples below, this adenosine can be substituted with any other natural or synthetic nucleotide, any modifications thereof and any derivatives thereof in some other embodiments.

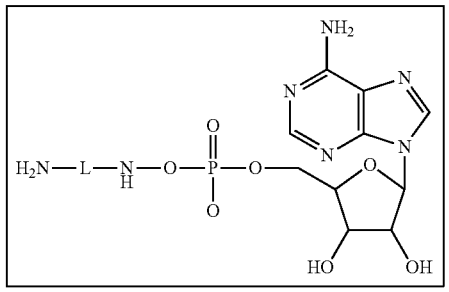

In some embodiments, various lengths of linkers at this position may have the following structures (exemplified with the Adenosine):

1. Ethylenediamine (2 Carbon Bond Length Separation)

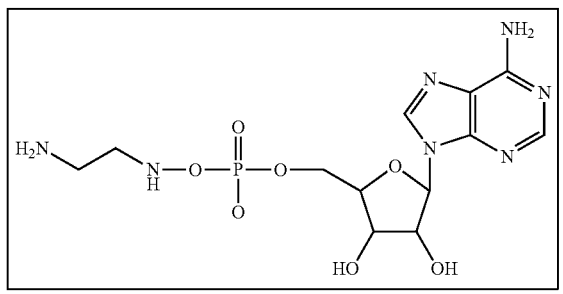 [SMILES: NCCNOP(=O)(O)OCC1OC(n2cnc3c(N)ncnc32)C(O)C1O]

2. Pentanediamine (5 Carbon Bond Length Separation)

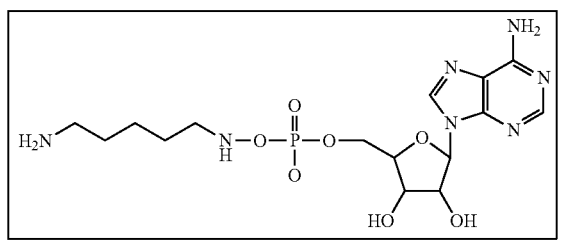 [SMILES: NCCCCCNOP(=O)(O)OCC1OC(n2cnc3c(N)ncnc32)C(O)C1O]

3. Length Equivalent to 13 Carbon Bond Length Separation

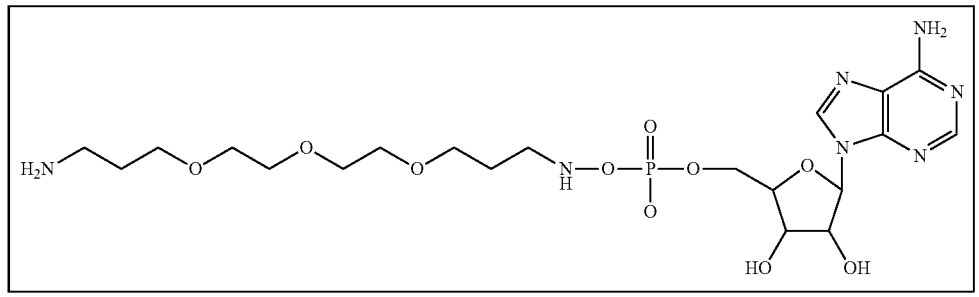 [SMILES: NCCCOCCOCCOCCCNOP(=O)(O)OCC1OC(n2cnc3c(N)ncnc32)C(O)C1O]

Thus in some embodiments, the linkers thus selected can be:
1. Easily available;
2. Easy to link and cleave (please refer the probable protocols below); and/or
3. Not to interact with the polymerase and the polynucleic acid strand and/or not affect nucleotide polymerization and growth of a nascent nucleotide polymer.

The reporter moiety: As used herein a "reporter moiety" is a molecule or molecules that are easily detected by a biosensor or other detection method (such as by eye) and are attached to biomolecules, or probes, or primers that detect or amplify molecules of interest that are normally difficult to detect without the presence of the reporter moiety 'reporting' on its presence. The reporter moieties can be any charged molecule, group of charged molecules and even many charged molecules arranged dendritically. The reporting mode is their charge, which is detected by sensitive charge detection biosensors, such as nanowire/nanotube FETS, nanopores and other piezoelectric biosensors. In some embodiments, the reporter moieties can be associated with the other properties like the chromophoric nature for enabling their detection by UV or visible detector or the fluorescent nature making them to be detected by the fluorimetric detection. Furthermore, the mass of the reporter moiety can be exploited using biosensors that can detect mass, such a surface Plasmon resonance biosensors and cantalivers.

The charge on the reporter: certain embodiments of the present invention describe the reporter moiety to carry a large charge mass. In one embodiment, the reporter moiety may introduce a higher charge mass to the synthetic nucleotide than the charge mass of the nucleotide or its derivative, which is present in the synthetic nucleotide. However, in another embodiment, the charge mass introduced by the reporter moiety can be substantially equal to or less than the charge mass of the nucleotide or its derivative, which is present in the synthetic nucleotide. Some non-limiting and illustrative examples of a reporter moiety are provided in this specification. These examples are provided only for the illustration purpose and therefore should not be considered to limit the scope of the invention. The chemical structure and/or dimension (e.g. length, size, and mass of a molecule used as a reporter moiety) of a reporter moiety may not be restricted as long as the reporter moiety is configured to provide a charge mass to the synthetic nucleotide and also not to affect polymerization reaction of nucleotides partially or entirely.

The charge on the moiety can be positive or negative. Taking into consideration the nature of linkage, the following provides some aspects of the selection of charge that can be possibly used in some embodiments of the present disclosure.

Positive charge: In some embodiments, the large number of positive charges can generally be induced on the reporter moiety through the incorporation of tertiary amino groups on the aromatic or aliphatic skeleton. In such embodiments, in turn in the acidic pH (less than 7), these groups may acquire the positive charges making them detectable.

Negative charges: In some other embodiments, the negative charges can generally be induced on the reporter moiety through the incorporation of alcohol hydroxyl and/or phenolic hydroxy functionalities on the aromatic or aliphatic skeleton. Given below are some of the proposed reporter moieties which meet the above mentioned criteria. The fragments listed below may be available and able to link to the linker through the amino terminal. The additional advantage could be that the reagents that are proposed for the phosphoramidate linkage formation may be the same as this amide linkage formation (Therefore reducing costs of the system further).

Moreover, at least in part due to the stability of this linkage to the alkaline pH (above 7), the process of induction of negative charge would be of no or substantially small interference.

For the purpose of illustration, the following three non-limiting examples are presented. These examples are provided only for the purpose of illustration and therefore should not be considered to limit the scope of the invention. As such, any modifications on the following examples are certainly included in the scope of the invention. For example, any substitution of one or more groups (e.g. —OH, =O, COOH, and others) linked to the examples can be practiced. Also oligomerization or polymerization of one of more of the following examples can also be permitted. Further any other chemical structure or molecule with various dimensions (e.g. length, size, and mass of the reporter moiety) can be used as a reporter moiety if such chemical structure or molecule is configured to provide a charged mass to the synthetic nucleotide and also not to affect polymerization reaction of nucleotides partially or entirely.

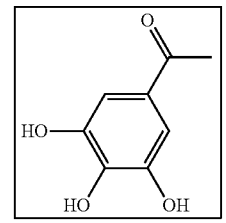

Potential charge-3

Reporter-1

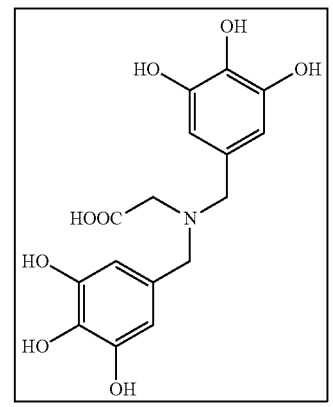

Potential charge-6

Reporter-2

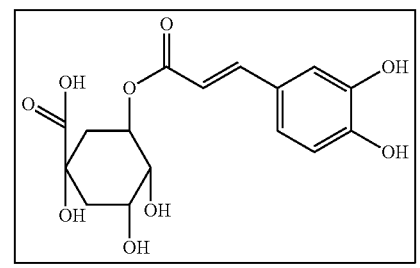

Potential charge-5

Reporter-3

After acquiring the charges, some of these reporters in certain embodiments may exist as follows,

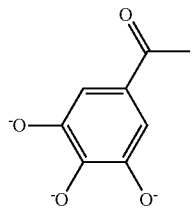

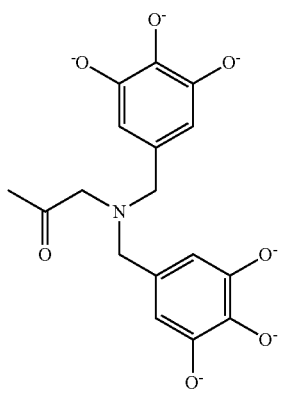

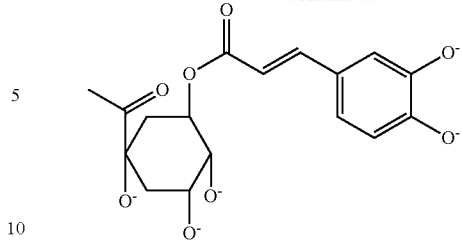

Whereas, the reporter-1 and reporter-3 may be available on shelf, reporter-2 may be custom synthesized.

The reporter moieties proposed can generally (be) thus:
1. Easily available or synthesizable;
2. bear a large charge;
3. Not costly; and/or
4. easy to link and cleave.

Final compounds (monomers): Based on the above propositions, the final structures of the nucleotides along with the linkers and the reporters would be as follows at least in certain parts of embodiments. The following examples of some final compounds are also provided for the purpose of illustration and therefore should not be considered to limit the scope of the invention. As described above, any variations permitted for a nucleotide or its derivative, a linker and a high charge mass reporter moiety are also permitted to a final compound. Thus, for the adenosine as a nucleotide at the 5'-phosphate terminal in some examples, if the linker is, say, C 13 equivalent (option 3 above), the various linkers would make the final structures looks as below:

One proposed final synthetic nucleotide-1 (note the reporter is in monomer form and this can be increased by aggregating these monomers to increase charge mass as required):

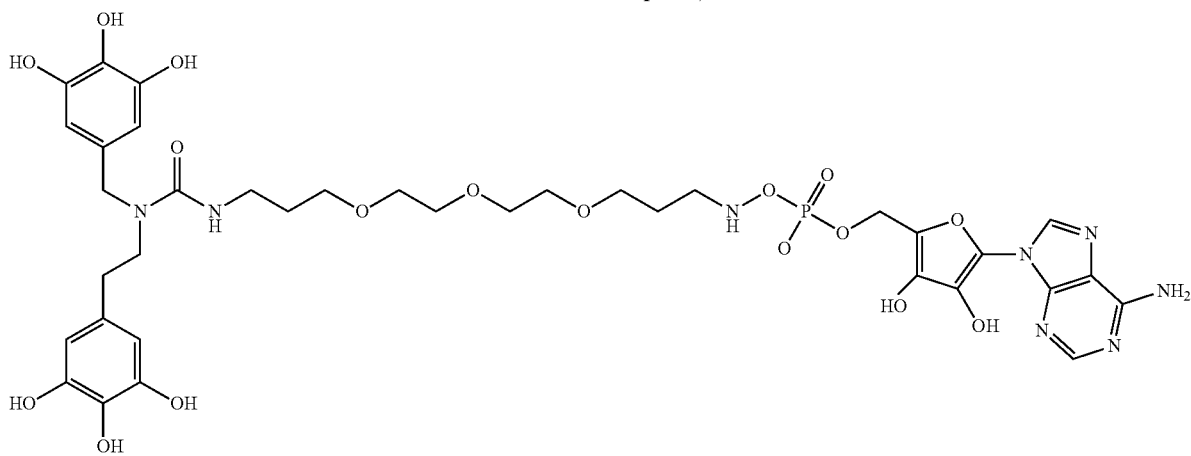

Another proposed synthetic nucleotide-2 (note the reporter is in monomer form and this can be increased by aggregating these monomers to increase charge mass as required):

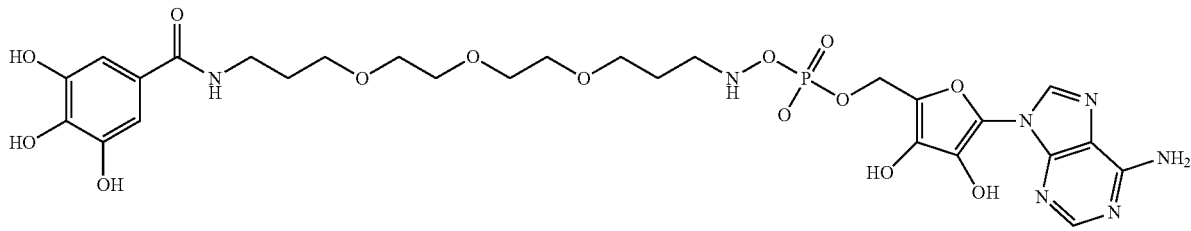 [SMILES: Nc1ncnc2c1ncn2-c1oc(COP(=O)(O)ONCCCOCCOCCOCCCNC(=O)c2cc(O)c(O)c(O)c2)c(O)c1O]

Still another proposed synthetic nucleotide-3 (note the reporter is in monomer form and this can be increased by aggregating these monomers to increase charge mass as required):

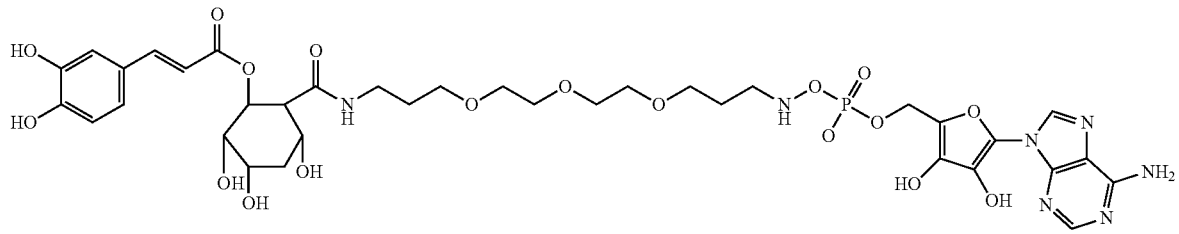 [SMILES: Nc1ncnc2c1ncn2-c1oc(COP(=O)(O)ONCCCOCCOCCOCCCNC(=O)C2C(O)CC(O)C(O)C2OC(=O)/C=C/c2ccc(O)c(O)c2)c(O)c1O]

The following is a non-limiting, illustrative example of synthesis protocols used in at least some embodiments:
1. Synthesis of 5'-phosphoramidates of Adenosine: (Linkage of Nucleotide with the diamine linker). Method of Chu et all can be used for synthesizing 5'-amino derivatives of adenosine phosphoramidate in which diamantes and adenosine monophosphate (AMP) can be dissolved in water. EDAC was added later on and was incubated at room temperature with constant stirring. The reaction was monitored till completion.
2. Synthesis of Final proposed structures: (Linkage of the diamine linker with reporter moiety). Method of Chu et all can be used for synthesizing 5'-amino derivatives of adenosine phosphoramidate in which diamines and adenosine monophosphate (AMP) can be dissolved in water. EDAC was added later on and then incubated at room temperature with constant stirring. The reaction was monitored till completion.

One advantage of the similar procedure is that it may work out for both the steps leading to the formation of final compounds as monomers.

In some illustrative examples of some embodiments, (see below) cleavage of the linkers and reporter moieties may need to be done. The linkages like phosphoramidates can generally be rather readily cleaved by the use of acids like Trifluoroacetic acid at an ambient temperature. By way of an illustrative example, the proposed synthetic nucleotide-2 demonstrated as a probable 3D view below. The aromatic ring at the bottom left of the molecule bears three hydroxy functions which could potentially get converted to the negative charge under slight alkaline conditions. Following is the 3D conformation of the Adenosine attached with the Reporter-1 through linker 3 and the related data.

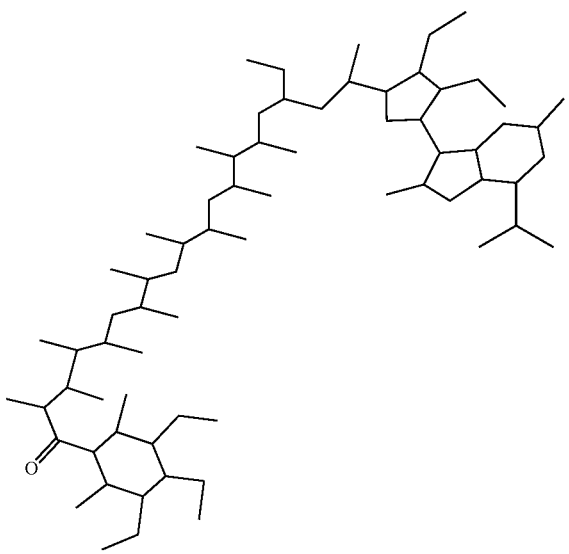 [SMILES: CCC(CC(C)C(C)C(C)CC(C)C(C)CC(C)C(C)CC(C)C(C)[C@H](C)C(C)C(=O)C1[C@H](C)[C@H](CC)C(CC)[C@@H](CC)[C@H]1C)C[C@H](C)[C@@H]1C[C@@H]([C@H]2C(C)CC3C2CC(C)C[C@H]3C(C)C)C(CC)[C@@H]1CC]

Approximate distance between the phosphoramidate and terminal charged atom may be about 20 angstroms, which could generally be sufficient to induce the charge potential in the surface for detection. This distance can further be altered with the further modifications in the phase at least in part by changing the linker lengths. The charge on the terminal reporter moieties can also be changed by the variations in the chemistry of reporter moieties.

In one embodiment, the reporter composition recited in the appended claims comprises any nucleotide with a cleavable linker molecule attached to a high charge mass moiety, wherein the synthetic nucleotide (otherwise referred to as the reporter composition) has a charge that is sufficient to cause a detectable change in the property of a sensitive detection nanostructure, when the reporter composition is operably coupled to the nanostructure (as for example, by addition of the synthetic nucleotide (reporter composition) to a nascent chain during a sequencing by synthesis procedure).

EXAMPLES

The following description is an illustrative example of some embodiments of the present disclosure.

Example 1

DNA Sequencing

The sequencing methodology in one example may not use fluorescence and expensive sensitive cameras, but instead may detect the addition of the synthetic nucleotides described in some aspects of the present disclosure, at least in part by sensing the electrical charge of reporter moiety, using sensitive nanostructures that may be capable of detecting a build up of charge mass at, or near, their surface. When a new nucleotide is added to the growing polymer in a sequencing by synthesis reaction, the charge density at, or near the surface of the sensitive nanostructure may increase and this can be detected by a change in property in the sensitive detection nanostructure (for instance, if using a nanowire, or carbon nanotube, as the detecting structure, an increase in charge caused by the addition of a nucleotide close to its surface may be detected by a change in resistance in the wire, due to a phenomenon called the field effect). However, as the polymer grows, the signal may diminish as the charges carried by the nucleotides being added may be too far away from the sensitive nanostructure (e.g. nanowire) to illicit a change in property of the sensitive detection nanostructure and no signal may be observed. Therefore, the 'read length' (amount of sequence data that is able to be obtained by this method of nucleotide sequencing) can be limited.

As used herein this particular example, a "sensitive detection nanostructure" can be any structure (nanoscale or not) which can be capable of detecting any change in charge at, or near it's surface and at any point may have at least one cross-sectional dimension less than about 500 nanometers, typically less than about 200 nanometers, more typically less than about 150 nanometers, still more typically less than about 100 nanometers, still more typically less than about 50 nanometers, even more typically less than about 20 nanometers, still more typically less than about 10 nanometers, and even less than about 5 nanometers. In other embodiments, at least on of the cross-sectional dimensions can generally be less than about 2 nanometers, or about 1 nanometer. In one set of embodiments the sensitive detection nanostructure can have at least one cross-sectional dimension ranging from about 0.5 nanometers to about 200 nanometers.

The properties of a sensitive detection nanostructure may change in response to surface, or near surface charge in a way that may be measurable via piezoelectric measurements, electrochemical measurement, electromagnetic measurement, photodetection, mechanical, measurement, acoustic measurement, gravimetric measurement and the like. An example of a sensitive detection nanostructure may include, but not limited to, two dimension field effect transistors, a cantalevers, nanowires, carbon nanotubes, and all piezoelectric macro-, micro-, nano-, pico-, zempto-, or smaller structures.

Certain embodiments of the present disclosure may address this limitation, at least in part by using synthetic nucleotides that may comprise normal nucleotides, with a high negative (or positive) charge mass reporter moiety attached via a linker molecule (for instance, attached to the 5' phosphate group), with the linker length increasing as the reaction progresses. This charge mass can be designed to 'reach down' to the sensitive nanostructure (e.g. nanowire) to cause a change in property of the sensitive detection nanostructure (e.g. a field effect or other piezo-electric change in the structure depending on the sensitive detection nanostructure used). To enable a good quality control measure and to ensure long read lengths by eliminating the build up of many reporter moieties which would cause an ever increasing field effect, these reporter moieties can be cleaved at least in certain embodiments, to allow for the addition of the next nucleotide in the sequencing by synthesis sequence.

Therefore, in some embodiments the cyclical reaction may comprise at least some or whole of the following entire or partial series of events:
1. The template ssDNA molecule to be sequenced can be either ligated to the sensitive detection nanostructure and a primer added, bind to a pre-immobilized primer sequence on the sensitive detection nanostructure, or uncoiled and elongated in a microfluidics channel arrayed with sensitive detection nanostructures.
2. The sensitive detection nanostructures can be washed with water, or a low salt buffer (such as 1×SSC)
3. A measure of the sensitive detection nanostructure can be made.
4. A mixture containing one synthetic nucleotide, the polymerase and other elements required for the polymerization reaction can be added. In one example, if the nucleotide added is complimentary to the base on the minus strand immediately after the primer sequence, it maybe incorporated into the growing chain by the polymerase.
5. The reaction can then be washed with either water or a low salt buffer (such as 1×SSC).
6. A measure of the sensitive detection nanostructure can be made which can observe the effect caused by the high charge mass of the reporter moiety.
7. The reporter moiety can then be cleaved (for instance by an acid solution or enzymatically).
8. Points 2 through 7 can be repeated for each of the four nucleotides. And this can be repeated repeatedly until a clear signal may degrade.

For some embodiments wherein the template molecule is immobilized to, or bound to a probe that can be in turn immobilized to the sensitive detection nanostructure, the linker lengths that attach the high charge reporter moiety to the synthetic nucleotides may increase to enable the charge to 'reach down' to the sensitive detection nanostructure to exert an effect. This may be necessary at least in some embodiments as the growing nucleotide polymer may move the next nucleotide addition site farther and farther from the sensitive detection nanostructure as the sequencing by synthesis reaction may progress.

For some other embodiments wherein the template molecules is not immobilized to the sensitive detection nanostructure, or hybridized to a primer/probe that can be in turn immobilized to the sensitive detection nanostructure, and can be instead free or immobilized horizontally across a cluster of sensitive detection nanostructures, a single linker length can be used for each of the cycle reactions.

Example 2

Primer Extension

In some embodiments, the synthetic nucleotides described in some aspects of the present disclosure for primer extension experiment wherein the detection is performed on electrical biosensors (nanowire/nanotube FETs, 2D FETS, nanopores, piezo-electric films/surfaces, etc). Primer extension is generally defined as a technique that can map or determine a 5' end of DNA or RNA. For example, primer extension can be used to determine the start site of the transcription start site for a gene. This technique generally requires a labelled primer, which is complementary to a region near the 3' end of the target gene. The primer is allowed to anneal to the transcript of the target gene and reverse transcriptase is used to synthesize complementary cDNA to the transcript until it reaches the 5' end of the transcript. By running the product on a polyacrylamide gel, it can be possible to determine the transcriptional start site, as the length of the sequence on the gel represents the distance from the start site to the labelled primer. During the synthesis of cDNA, the synthetic nucleotides disclosed in this application can be used and added to the nascent cDNA chain. The addition of the specific synthetic nucleic acid (e.g. deoxynucleotide with Adenine, Guanine, Thymidine, or Cystine) can be detected by a nanosensor. The nanosensor, which is further described below can be attached to the primer so that the nascent cDNA chain may be attached to the nanosensor in some embodiments. Alternatively, in some other embodiments, the transcript of the target sequence may be attached to the nanosensor (e.g. nanowires, nanotubes, nanobeads, nanopores, nanogaps and others).

Biosensors

As used in various embodiments, a biosensor is generally a device for the detection of an analyte that combines a biological component with a physicochemical detector component. In some embodiments, it may comprise three parts: 1. the sensitive biological element (biological material (eg. tissue, microorganisms, organelles, cell receptors, enzymes, antibodies, nucleic acids, etc), a biologically derived material or biomimic). The sensitive elements can be created by biological engineering; 2. the transducer or the detector element (works in a physicochemical way; optical, piezoelectric, electrochemical, etc.) that transforms the signal resulting from the interaction of the analyte with the biological element into another signal (i.e., transducers) that can be more easily measured and quantified; 3. associated electronics or signal processors that is primarily responsible for the display of the results in a user-friendly way. In some other examples, the signal processing unit may further comprise one or more of a signal sensing unit, a signal recording unit, a data processing unit, and a data reporting unit.

Nanostructures

As used in various embodiments, a nanowire is an elongated nanoscale semiconductor which, at any point along its length, has at least one cross-sectional dimension and, in some embodiments, two orthogonal cross-sectional dimensions less than 500 nanometers, preferably less than 200 nanometers, more preferably less than 150 nanometers, still more preferably less than 100 nanometers, even more preferably less than 70, still more preferably less than 50 nanometers, even more preferably less than 20 nanometers, still more preferably less than 10 nanometers, and even less than 5 nanometers. In other embodiments, the cross-sectional dimension can be less than 2 nanometers or 1 nanometer. In one set of embodiments the nanowire has at least one cross-sectional dimension ranging from 0.5 nanometers to 200 nanometers. Where nanowires are described having a core and an outer region, the above dimensions relate to those of the core. The cross-section of the elongated semiconductor may have any arbitrary shape, including, but not limited to, circular, square, rectangular, elliptical and tubular. Regular and irregular shapes are included. A non-limiting list of examples of materials from which nanowires of the invention can be made appears below.

Nanotubes are a class of nanowires that may find use in the invention and, in one embodiment, devices of the invention include wires of scale commensurate with nanotubes. As used herein, a "nanotube" is a nanowire that has a hollowed-out core, and includes those nanotubes know to those of ordinary skill in the art. A "non-nanotube nanowire" is any nanowire that is not a nanotube. In one set of embodiments of the invention, a non-nanotube nanowire having an unmodified surface (not including an auxiliary reaction entity not inherent in the nanotube in the environment in which it is positioned) is used in any arrangement of the invention described herein in which a nanowire or nanotube can be used. A "wire" refers to any material having a conductivity at least that of a semiconductor or metal. For example, the term "electrically conductive" or a "conductor" or an "electrical conductor" when used with reference to a "conducting" wire or a nanowire refers to the ability of that wire to pass charge through itself. Preferred electrically conductive materials have a resistivity lower than about $10^{-3}$, more preferably lower than about $10^{-4}$, and most preferably lower than about $10^{-6}$ or $10^{-7}$ ohm-meters.

Nanopore generally has one or more small holes in an electrically insulating membrane that can be used as a single-molecule detector. In some cases, it can be a biological protein channel in a high electrical resistance lipid bilayer or a pore in a solid-state membrane. Nanopore is generally a spherical structure in a nanoscale size with one or more pores therein. According to some aspects, a nanopore is made of carbon or any conducting material.

Nanobead is generally a spherical structure in a nanoscale size. The shape of nanobead is generally spherical but can also be circular, square, rectangular, elliptical and tubular. Regular and irregular shapes are included. In some examples, the nanobead may have a pore inside.

Nanogap is generally used in a biosensor that consists of separation between two contacts in the nanometer range. It senses when a target molecule, or a number of target molecules hybridize or binds between the two contacts allowing for the electrical signal to be transmitted through the molecules.

The foregoing nanostructures, namely, nanowire, nanotube, nanopore, nanobead, and nanogap are described to provide the instant illustration of some embodiments, and not for limiting the scope of the present invention. In addition to the foregoing examples, any nanostructure that has a nanoscale size and is suitable to be applied to nucleic acid detection methods and apparatus as disclosed in the application should also be considered to be included in the scope of the invention.

In general, sensing strategies for use with nanostructures or nanosensors to detect molecules and compounds is to sense changes in the charge at, or near their surfaces, or across a nanogap or nanopore, which cause a measurable change in their properties (such as field effect transistors, nanogaps, or piezoelectric nanosensors) to detect & quantify target nucleic acids (DNA, RNA, cDNA, etc).

Aspects of the invention provide a nanowire or nanowires preferably forming part of a system constructed and arranged to determine an analyte in a sample to which the nanowire(s) is exposed. "Determine", in this context, means to determine the quantity and/or presence of the analyte in the sample. Presence of the analyte can be determined by determining a change in a characteristic in the nanowire, typically an electrical characteristic or an optical characteristic. E.g. an analyte causes a detectable change in electrical conductivity of the nanowire or optical properties. In one embodiment, the nanowire includes, inherently, the ability to determine the analyte. The nanowire may be functionalized, i.e. comprising surface functional moieties, to which the analytes binds and induces a measurable property change to the nanowire. The binding events can be specific or non-specific. The functional moieties may include simple groups, selected from the groups including, but not limited to, —OH, —CHO, —COOH, —SO$_3$H, —CN, —NH$_2$, —SH, —COSH, COOK, halide; biomolecular entities including, but not limited to, amino acids, proteins, sugars, DNA, antibodies, antigens, and enzymes; grafted polymer chains with chain length less than the diameter of the nanowire core, selected from a group of polymers including, but not limited to, polyamide, polyester, polyimide, polyacrylic; a thin coating covering the surface of the nanowire core, including, but not limited to, the following groups of materials: metals, semiconductors, and insulators, which may be a metallic element, an oxide, an sulfide, a nitride, a selenide, a polymer and a polymer gel. In another embodiment, the invention provides a nanowire and a reaction entity with which the analyte interacts, positioned in relation to the nanowire such that the analyte can be determined by determining a change in a characteristic of the nanowire.

Field Effect Transistor (FET)

Field effect generally refers to an experimentally observable effect symbolized by F (on reaction rates, etc.) of intramolecular coulombic interaction between the centre of interest and a remote unipole or dipole, by direct action through space rather than through bonds. The magnitude of the field effect (or 'direct effect') may depend on the unipolar charge/dipole moment, orientation of dipole, shortest distance between the centre of interest and the remote unipole or dipole, and on the effective dielectric constant. This is exploited in transistors for computers and more recently in DNA field-effect transistors used as nanosensors.

Field-effect transistor (FET) is generally a field-effect transistor, which may use the field-effect due to the partial charges of biomolecules to function as a biosensor. The structure of FETs can be similar to that of metal-oxide-semiconductor field-effect transistor (MOSFETs) with the exception of the gate structure which, in biosensor FETs, may be replaced by a layer of immobilized probe molecules which act as surface receptors. When target biomolecules hybridize or bind, to the receptors, the charge distribution near the surface changes, which in turn modulates current transport through the semiconductor transducer (e.g. nanowire).

Biological Samples

The term sample or biological sample generally refers to any cell, tissue, or fluid from a biological source (a "biological sample"), or any other medium, biological or non-biological, that can be evaluated in accordance with the invention including, such as serum or water. A sample includes, but is not limited to, a biological sample drawn from an organism (e.g. a human, a non-human mammal, an invertebrate, a plant, a fungus, an algae, a bacteria, a virus, etc.), a sample drawn from food designed for human consumption, a sample including food designed for animal consumption such as livestock feed, milk, an organ donation sample, a sample of blood destined for a blood supply, a sample from a water supply, or the like. One example of a sample is a sample drawn from a human or animal to determine the presence or absence of a specific nucleic acid sequence.

Nucleic Acid or Oligonucleotide

The terms nucleic acid or oligonucleotide or grammatical equivalents herein refer to at least two nucleotides covalently linked together. A nucleic acid of the present invention is preferably single-stranded or double stranded and will generally contain phosphodiester bonds, although in some cases, as outlined below, nucleic acid analogs are included that may have alternate backbones, comprising, for example, phosphoramide (Beaucage et al. (1993) Tetrahedron 49(10):1925) and references therein; Letsinger (1970) J. Org. Chem. 35:3800; Sprinzl et al. (1977) Eur. J. Biochem. 81: 579; Letsinger et al. (1986) Nucl. Acids Res. 14: 3487; Sawai et al. (1984) Chem. Lett. 805, Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 131:2321, O-methylphophoroamidite linkages (see Eckstein, Oligonucleotides and Analogues: A Practical Approach, Oxford University Press), and peptide nucleic acid backbones and linkages (see Egholm (1992) J. Am. Chem. Soc. 114:1895; Meier et al. (1992) Chem. Int. Ed. Engl. 31: 1008; Nielsen (1993) Nature, 365: 566; Carlsson et al. (1996) Nature 380: 207). Other analog nucleic acids include those with positive backbones (Denpcy et al. (1995) Proc. Natl. Acad. Sci. USA 92: 6097; non-ionic backbones (U.S. Pat. Nos. 5,386,023, 5,637,684, 5,602,240, 5,216,141 and 4,469,863; Angew. (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghui and P. Dan Cook; Mesmaeker et al. (1994). Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghui and P. Dan Cook. Nucleic acids containing one or more carbocyclic sugars are also included within the definition of nucleic acids (see Jenkins et al. (1995). Chem. Soc. Rev. pp. 169-176). Several nucleic acid analogs are described in Rawls, C & E News Jun. 2, 1997 page 35. These modifications of the ribose-phosphate backbone may be done to facilitate the addition of additional moieties such as labels, or to increase the stability and half-life of such molecules in physiological environments.

Sensing Strategies

In one aspect of the invention, a biological material configured to bind a nanostructure is a nucleic acids. Such nucleic acids may include DNA, RNA, and any derivatives thereof. In one embodiment, the biological material is DNA. When DNA is attached to the nanostructure, the number of nucleotides may range from 5 bases to 100 bases. In some embodiments, the number of DNA nucleotides may be 7 bases, 10 bases, 15 bases, 20, bases, 25 bases, 30 bases, 35 bases, 40 bases, 45 bases, 50 bases, 60 bases, 70 bases, 80 bases, 90 bases and 100 bases. In some other embodiments, ribonucleic acids and any nucleic acid derivatives may be attached to the nanostructure. In still some other embodiments, DNA, RNA and its derivatives may be used simultaneously. Therefore in one example, DNA sequences may be attached to the nanostructure, whereas in another example, RNA sequences may be attached to the nanostructure, still another example, nucleic acid derivatives such as a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof may be attached to the nanostructure. In some other examples, nucleotide sequences comprising DNA and RNA, DNA and nucleic acid derivatives, RNA and derivatives, and DNA, RNA and derivatives may be attached to the nanostructure.

In another aspect of the invention, a nanostructure is conducting and can sense the electric charge, which is originated from the synthetic nucleotide as disclosed in this application, at its surface, vicinity, inner tubes and/or the pores therein. One of key aspects of any diagnostic device is the ability to perform accurate detection of biomolecules with the performance determined by how well it detects specifically (i.e. a low false positive rate) and sensitively (i.e. a low false negative rate). Nanosensors that can sense changes in the charge at, or near their surfaces, or across a nanogap or nanopore, which cause a measurable change in their properties, at least in part due to the target molecule binding to a probe immobilized on or near the nanostructures, provide a method for ultra-sensitive detection without or with limited use of the need for labels (expensive chemicals that can be bound to the biomolecule or molecule of interest to enable detection devices to 'sense' them).

The present disclosure generally relates to molecular biological protocols and sensing strategies for use with nanosensors that may detect molecules and compounds by sensing changes in the charge at, or near their surfaces, or across a nanogap or nanopore, which cause a measurable change in their properties (such as field effect transistors, nanogaps, or piezoelectric nanostructures or nanosensors) to detect & quantify target nucleic acids (DNA. RNA, cDNA, etc). The basic function of these biosensors may require that a nucleotide polymer probe (or synthetic nucleotide polymer such as PNA, Morpholinos, etc) be immobilized on, or near to, the nanostructures and the build up of target molecules binding to the probe can cause an increase in charge density at or near the surface of the nanostructures or nanosensors, due to the charge of the probe. For instance, an amplified PCR fragment binding to a probe (with a reverse complimentary sequence to the target nucleotide polymer), immobilized on a nanowire can cause a measurable change conductance ($\Delta G$) due to the increase in negative charge at, or near to the nanowire's surface, due to a phenomena called the field effect. In some embodiments, the electric charge present in the synthetic nucleotide, which is originated from the nucleotide itself and the high charge mass reporter moiety, can be detected by the nanostructures/nanosensors.

These nanosensors may offer the potential for sensitive and dynamic detection of biomolecules, however, this sensitivity may bring with it a number of issues. For instance, natural fluctuations of charge at the surface, within the sample matrix may cause noise, in part due to the flanking sequences of target nucleotide polymer molecules (i.e. the over hanging sequences that don't bind to the probes). Furthermore, if many target molecules are being detected at the same time on an array of nanosensors, it would be favorable to standardize the size and therefore charge mass, of each of these molecules to allow for more stringent comparisons and quality control. Moreover, having a standard size for all target molecules allows for standardization of probe hybridization conditions in the array assay design.

Biosensor System

Biosensor is generally an analytical device that may convert molecular events into electrical signals. The nanostructures used in a biosensor are generally used to detect components of interest such as nucleic acids. Biosensors can generally operate in the liquid or gas phase, opening up an enormous variety of applications, e.g., for integrated devices and for downstream applications. Therefore, the biosensors can be manufactured inexpensively and portable and are optionally used as implantable detection and monitoring devices. Alternatively, the biosensor can be coupled with other high-resolution apparatus such as mass-spectroscopy and provide further information including the detection of presence, abundance and/or structural variation of the target biomolecules.

One aspect of the invention involves a sensing element of a biosensor, which can be an electronic sensing element, and a nanowire able to detect the presence, or absence, of an analyte in a sample (e.g. a fluid sample) containing, or suspected of containing, the analyte. Nanoscale sensors of the invention may be used, for example, in chemical applications to detect pH or the presence of metal ions; in biological applications to detect a protein, nucleic acid (e.g. DNA, RNA, etc.), a sugar or carbohydrate, and/or metal ions; and in environmental applications to detect pH, metal ions, or other analytes of interest.

Another aspect of the invention involves an article of a biosensor comprising a sample exposure region and a nanowire able to detect the presence of absence of an analyte. The sample exposure region may be any region in close proximity to the nanowire wherein a sample in the sample exposure region addresses at least a portion of the nanowire. Examples of sample exposure regions include, but are not limited to, a well, a channel, a microchannel, and a gel. In preferred embodiments, the sample exposure region holds a sample proximate the nanowire, or may direct a sample toward the nanowire for determination of an analyte in the sample. The nanowire may be positioned adjacent to or within the sample exposure region. Alternatively, the nanowire may be a probe that is inserted into a fluid or fluid flow path. The nanowire probe may also comprise a micro-needle and the sample exposure region may be addressable by a biological sample. In this arrangement, a device that is constructed and arranged for insertion of a micro-needle probe into a biological sample will include a region surrounding the micro-needle that defines the sample exposure region, and a sample in the sample exposure region is addressable by the nanowire, and vice-versa. Fluid flow channels can be created at a size and scale advantageous for use in the invention (microchannels) using a variety of techniques such as those described in International Patent Publication No. WO 97/33737, published Sep. 18, 1997, and incorporated herein by reference.

In another aspect of the invention, an article may comprise a plurality of nanowires able to detect the presence or absence of a plurality of one or more analytes. The individual nanowires may be differentially doped as described above, thereby varying the sensitivity of each nanowire to the analyte. Alternatively, individual nanowires may be selected based on their ability to interact with specific analytes, thereby allowing the detection of a variety of analytes. The plurality of nanowires may be randomly oriented or parallel to one another. Alternatively, the plurality of nanowires may be oriented in an array on a substrate.

Where a detector is present, any detector capable of determining a property associated with the nanowire can be used. The property can be electronic, optical, or the like. An electronic property of the nanowire can be, for example, its conductivity, resistivity, etc. An optical property associated with the nanowire can include its emission intensity, or emission wavelength where the nanowire is an emissive nanowire where emission occurs at a p-n junction. For example, the detector can be constructed for measuring a change in an electronic or magnetic property (e.g. voltage, current, conductivity, resistance, impedance, inductance, charge, etc.) can be used. The detector typically includes a power source and a voltmeter or amp meter. In one embodiment, a conductance less than 1 nS can be detected. In a preferred embodiment, a conductance in the range of thousandths of a nS can be detected. The concentration of a species, or analyte, may be detected from less than micromolar to molar concentrations and above. By using nanowires with known detectors, sensitivity can be extended to a single molecule. In one embodiment, an article of the invention is capable of delivering a stimulus to the nanowire and the detector is constructed and arranged to determine a signal resulting from the stimulus. For example, a nanowire including a p-n junction can be delivered a stimulus (electronic current), where the detector is constructed and arranged to determine a signal (electromagnetic radiation) resulting from the stimulus. In such an arrangement, interaction of an analyte with the nanowire, or with a reaction entity positioned proximate the nanowire, can affect the signal in a detectable manner. In another example, where the reaction entity is a quantum dot, the quantum dot may be constructed to receive electromagnetic radiation of one wavelength and emit electromagnetic radiation of a different wavelength. Where the stimulus is electromagnetic radiation, it can be affected by interaction with an analyte, and the detector can detect a change in a signal resulting therefrom. Examples of stimuli include a constant current/voltage; an alternating voltage, and electromagnetic radiation such as light.

Another aspect of the present invention provides an article comprising a nanowire and a detector constructed and arranged to determine a change in an electrical property of the nanowire. At least a portion of the nanowire is addressable by a sample containing, or suspected of containing, an analyte. The phrase "addressable by a fluid" is defined as the ability of the fluid to be positioned relative to the nanowire so that an analyte suspected of being in the fluid is able to interact with the nanowire. The fluid may be proximate to or in contact with the nanowire.

In some embodiments, the nanostructures can be assembled into a plurality of parallel arrays such as microcolumns at higher densities than is and in a format compatible with currently available micro-fluidic systems. The nanostructure arrays optionally comprise a plurality of nanostructures such as nanowires, nanotubes, nanopores, nanobeads, nanogaps, or a combination thereof. Each nanostructure of the array can be electrically connected, e.g., via two or more electrodes to a battery for applying a voltage across the nanowire and a detector, for detection of any changes in conductance of the nanowire. Alternatively, each nanostructure separately receives electricity or only a portion of nanostructures arrayed together may be electrically connected.

A single detector or a combination of detectors is optionally used to detect the signal from the array of nanowires. For example, each nanowire linked to a probe comprising different target sequence, which may be bound to a same or different probe, is optionally detected separately, such that a spatial array of a plurality of nanowires can be used to quickly identify, e.g., a plurality of different nucleotide sequences present in a biological sample such as blood. In some examples, a plurality of patches of nanostructures are prepared in the array and each patch presents different probes to detect multiple target sequences in a biological sample. Alternatively, in some other examples, an entire nanostructures present in the array may present same probes, thereby only one target sequence would be tested for its presence, abundance and/or variation in the sequence.

The detection by the nanostructure or nanosensor is generally a change in conductance of the nanostructure or of its environment. The signal can be expressed in terms of a change in the voltage across the nanostructure, or the current through the nanostructure. Such changes are typically detected electrically, e.g., with a voltmeter and/or a current meter. Alternatively, the signal is detected digitally. In one embodiment, a voltage is applied across a nanostructure, e.g., a nanowire, providing a steady state signal. When a binding event occurs on the probe attached to the nanostructure, the electric field in the vicinity of the nanostructure changes and the conductance of the nanostructure changes, producing a fluctuation or shift in the steady state signal. The signal may be detected, electrically or digitally, and provides real time detection of the event of interest.

Biosensor can also be integrated into a system for detecting a presence, level and/or variation of biomolecules. In one aspect, such system may include an electrical power supply, monitoring system for applying and measuring electrical current across the nanostructure element. In another aspect, such system may further include data processing capabilities to enable the programmed operation of the nanostructures and to receive, store, and provide useful analysis and display of the data that is obtained. In addition a computer system to process the obtained data as well as additional processor(s) may be integrated into a biosensor system if desired. The computer system or any additional elements present in a biosensor system may provide a software(s) for analyzing the data or for automatic operation and/or manual(s) to perform detection processes with a biosensor. Furthermore, any additional elements that may enhance the performance of a biosensor system can be added. A biosensor of the present invention can collect real time data.

Example 3

Hybridization Such as Microarrays

In still some other embodiments, the synthetic nucleotide disclosed in some aspects of the present disclosure can be used for hybridization procedures. Some non-limiting, illustrative examples of the hybridization procedures include a microarray for nucleonic acids as well as proteins. Further any other procedures that need hybridization and can determine presence, abundance or any structural variation of the target biomolecules can be included.

In one example, the probes used in a microarray can be attached to a medium such as nanosensors (e.g. nanowires, nanotubes, nanobeads, nanaopores, nanogaps, and other nanostructures). In some cases, the target nucleotide sequences obtained from the biological samples would be labeled and contacted with the probes. In such cases, the target nucleotide may incorporate the synthetic nucleotides thereby being labeled with "high charge mass". As such, the binding of the target sequences to the probes can be readily determined by the nanosensors that the probes are attached to. Moreover, the synthetic nucleotide disclosed in this application can be used, for example, in the methods of detecting presence, abundance and/or structural variation of nucleic acids as disclosed in the related application of the subject application, U.S. provisional application No. 61/094,017 filed on Sep. 3, 2008, the disclosures of which are hereby expressly incorporated by reference in their entirety and are hereby expressly made a portion of this application. As such, the use of the synthetic nucleotide of this application is not limited and can be further extended if applicable.

What is claimed is:

1. A reporter composition, comprising:
a nucleotide or its derivative;
a charged moiety; and
a linker molecule, wherein the linker molecule is attached to the nucleotide or its derivative and the charged moiety;
wherein the charged moiety comprises an electrical charge that is sufficient to change an electrical property of a sensitive detection nanostructure, when the reporter composition is operably coupled to the sensitive detection nanostructure,
wherein the charged moiety comprises one or more of the following groups, and derivatives and combinations thereof:

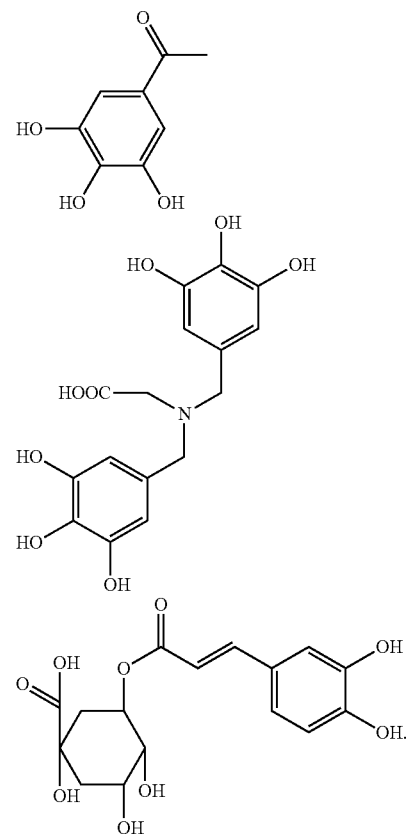

2. The reporter composition of claim 1, wherein the nucleotide or its derivative is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

3. The reporter composition of claim 1, wherein the linker molecule comprises a molecule of the following general formula:

wherein L comprises a linear or branched chain comprising an alkyl group, an oxy alkyl group, or the combination thereof.

4. The reporter composition of claim 3, wherein L comprises a linear chain comprising an alkyl group, an oxy alkyl group, or the combination thereof.

5. The reporter composition of claim 4, wherein a number of the alkyl group, the oxy alkyl group, or the combination thereof in the linear chain is 1 to 100.

6. The reporter composition of claim 5, wherein the number of the alkyl group, the oxy alkyl group, or the combination thereof in the linear chain is 1 to 75.

7. The reporter composition of claim 5, wherein the number of the alkyl group, the oxy alkyl group, or the combination thereof in the linear chain is 1 to 50.

8. The reporter composition of claim 5, wherein the number of the alkyl group, the oxy alkyl group, or the combination thereof in the linear chain is 1 to 25.

9. The reporter composition of claim 5, a number of the alkyl group, the oxy alkyl group, or the combination thereof in the linear chain is 1 to 1000.

10. The reporter composition of claim 5, a number of the alkyl group, the oxy alkyl group, or the combination thereof in the linear chain is more than 1000.

11. The reporter composition of claim 1, wherein the linker molecule is configured not to affect nucleotide polymerization by a polymerase.

12. The reporter composition of claim 1, wherein the electrical charge of the charged moiety is positive or negative.

13. The reporter composition of claim 1, wherein the electrical charge of the charged moiety is variable depending on pH.

14. The reporter composition of claim 1, wherein the charged moiety comprises an aromatic and/or aliphatic skeleton, wherein said skeleton comprises one or more of a tertiary amino group, an alcohol hydroxyl group, a phenolic hydroxy group, and any combinations thereof.

15. The reporter composition of claim 1, wherein a number of the groups, any derivatives thereof, and any combinations thereof in the charged moiety is 1 to 10.

16. The reporter composition of claim 1, wherein a number of the groups, any derivatives thereof, and any combinations thereof in the charged moiety is 11 to 50.

17. The reporter composition of claim 1, wherein a number of the groups, any derivatives thereof, and any combinations thereof in the charged moiety is 51 to 100.

18. The reporter composition of claim 1, wherein a number of the groups, any derivatives thereof, and any combinations thereof in the charged moiety is more than 100.

19. The reporter composition of claim 1, wherein the charged moiety is configured not to affect nucleotide polymerization by a polymerase.

20. The reporter composition of claim 1, wherein the linker molecule and/or the charged moiety is configured to be removable.

21. A reporter composition, comprising:

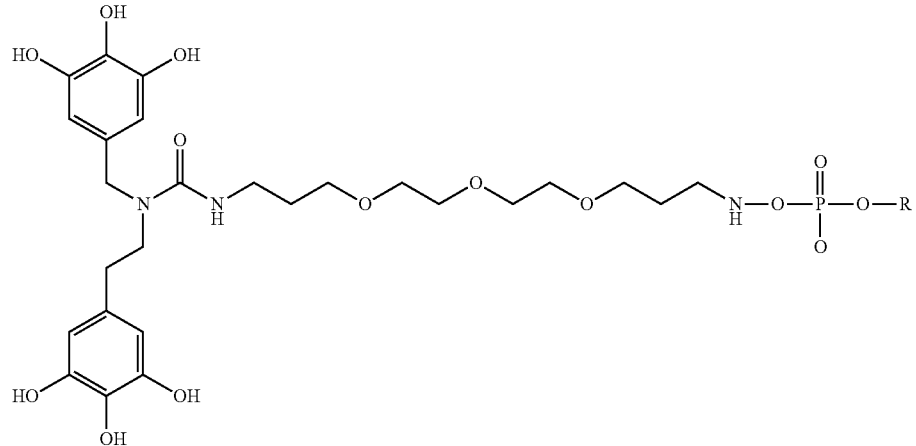

wherein R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

22. A reporter composition, comprising:

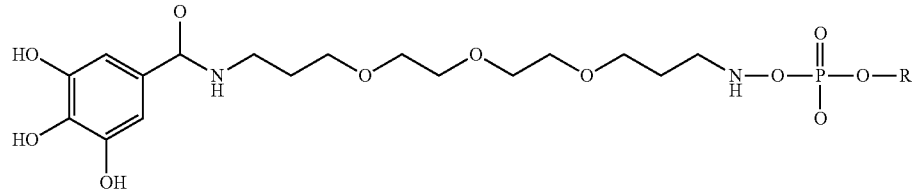

wherein R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

23. A reporter composition, comprising:

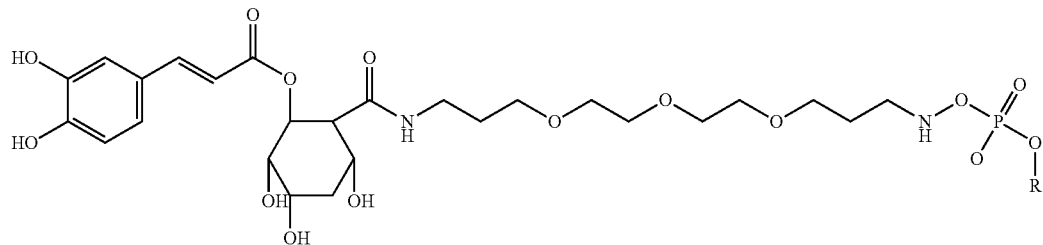

wherein R is selected from the group consisting of a deoxyribonucleotide, a ribonucleotide, a peptide nucleotide, a morpholino, a locked nucleotide, a glycol nucleotide, a threose nucleotide, any synthetic nucleotides, any isoforms thereof, and any derivatives thereof.

24. A kit for determining a nucleotide sequence, comprising the reporter composition of claim 1.

25. A method of synthesizing the reporter composition of claim 1, comprising:
generating a first covalent linkage between the nucleotide or its derivative and a first amine group of the linker, wherein a phosphate group, a sugar or a base of the nucleotide or its derivative is linked to the first amine group of the linker; and
generating a second covalent linkage between a second amine group of the linker and any functional group present in the charged moiety;
wherein the linker comprises at least two amine groups.

26. The method of claim 25, wherein the nucleotide or its derivative comprises a monophosphate group.

27. The method of claim 25, wherein the nucleotide or its derivative is selected from the group consisting of adenosine monophosphate (AMP), guanosine monophosphate (GMP), cytidine monophosphate (CMP), thymidine monophosphate (TMP), and uridine monophosphate (UMP).

28. A kit for determining a nucleotide sequence, comprising the reporter composition of claim 21.

* * * * *